(12) United States Patent
Li

(10) Patent No.: US 10,347,110 B1
(45) Date of Patent: Jul. 9, 2019

(54) RECLINING MECHANISM OR BED WITH BUILT-IN PRESSURE ALARM AND DYNAMIC THERAPEUTIC ADJUSTMENT CAPABILITIES

(71) Applicant: Tianfu Li, Bloomfield Hills, MI (US)

(72) Inventor: Tianfu Li, Bloomfield Hills, MI (US)

( * ) Notice: Subject to any disclaimer, the term of this patent is extended or adjusted under 35 U.S.C. 154(b) by 0 days.

(21) Appl. No.: 15/934,051

(22) Filed: Mar. 23, 2018

(51) Int. Cl.
*A61B 5/00* (2006.01)
*A61B 5/11* (2006.01)
*G08B 21/04* (2006.01)

(52) U.S. Cl.
CPC ........ *G08B 21/0461* (2013.01); *A61B 5/1113* (2013.01); *A61B 5/1116* (2013.01); *A61B 5/1126* (2013.01); *A61B 5/6831* (2013.01); *A61B 5/6887* (2013.01); *A61B 2562/0247* (2013.01); *A61B 2562/04* (2013.01)

(58) Field of Classification Search
None
See application file for complete search history.

(56) References Cited

U.S. PATENT DOCUMENTS

| | | | |
|---|---|---|---|
| 6,204,767 B1 | 3/2001 | Sparks | |
| 6,917,293 B2 | 7/2005 | Beggs | |
| 7,666,151 B2 | 2/2010 | Sullivan et al. | |
| 8,416,084 B2 | 4/2013 | Beltmann et al. | |
| 9,253,891 B2 | 2/2016 | Williams | |
| 9,668,927 B2 | 6/2017 | Campbell | |
| 9,767,667 B2 | 9/2017 | Sullivan et al. | |
| 2004/0104559 A1* | 6/2004 | Chen | A61H 3/04 280/642 |
| 2011/0138536 A1* | 6/2011 | Wernqvist | A61G 7/002 5/618 |
| 2012/0154155 A1 | 6/2012 | Brasch | |
| 2014/0257057 A1* | 9/2014 | Reis Cunha | A61B 5/1116 600/301 |
| 2015/0035671 A1 | 2/2015 | Williams | |
| 2015/0182400 A1* | 7/2015 | Meyer | A61G 7/018 5/710 |

FOREIGN PATENT DOCUMENTS

| | | |
|---|---|---|
| EP | 107058 A1 | 5/1984 |
| GB | 2538153 B | 11/2017 |
| WO | 2017039403 A1 | 3/2017 |

* cited by examiner

*Primary Examiner* — Thomas S McCormack
(74) *Attorney, Agent, or Firm* — Dinsmore & Shohl LLP

(57) ABSTRACT

A patient support and reclining device having a built in alarm and including an arrangement of sensors, timer and switches extending between the device and a separate connected control module for notifying when the patient is no longer supported upon the chair or recliner or when the patient has been supported in a static position to too long a period of time, thus notifying the caregiver of the necessity of repositioning in order to prevent the occurrence of bedsores and the like. The recliner device includes slaved or independent repositionable drives incorporated into the seat and back supports. The repositionable drives are communicated with the control module in order to reconfigure the patient support device, such as timed intervals to correspond with patient repositioning, such as of particular value to immobile or mobility limited individuals.

17 Claims, 10 Drawing Sheets

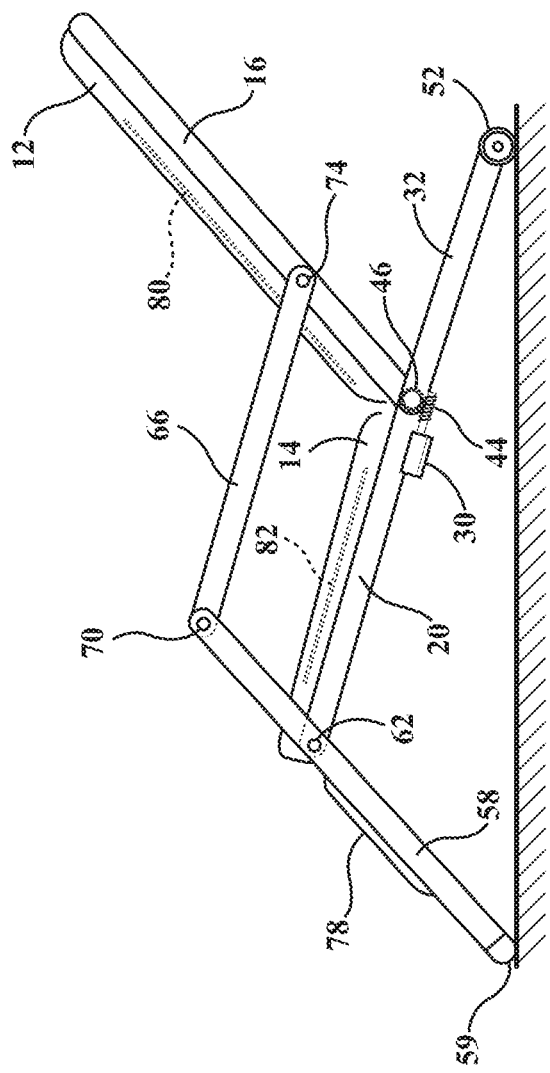
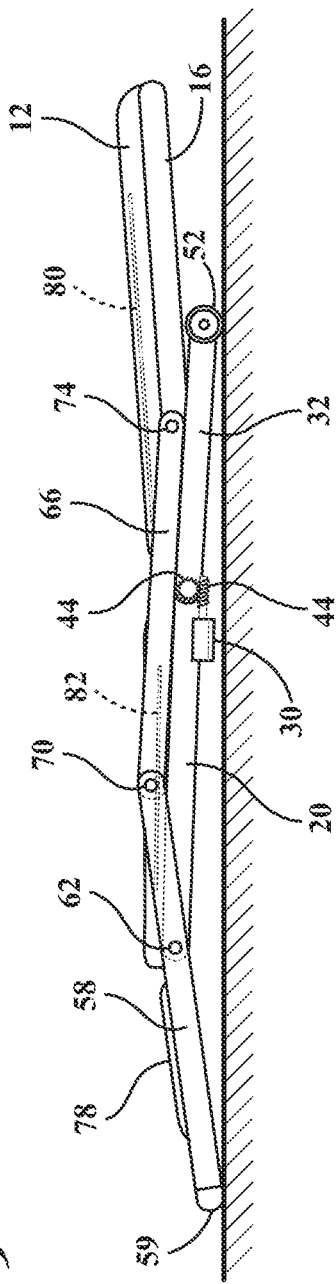
FIG. 8
FIG. 9

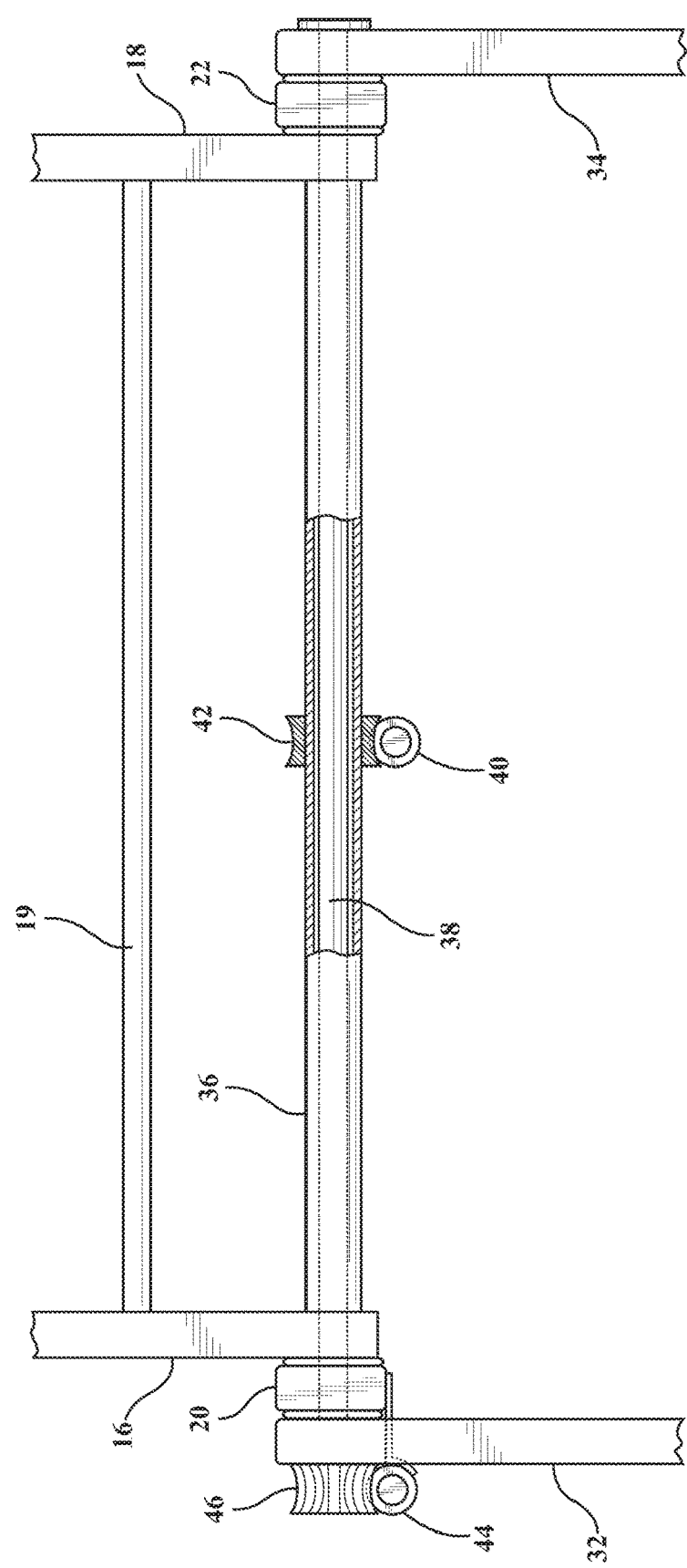

RECLINING MECHANISM OR BED WITH BUILT-IN PRESSURE ALARM AND DYNAMIC THERAPEUTIC ADJUSTMENT CAPABILITIES

FIELD OF THE INVENTION

The present invention relates generally to a patient supporting and reclining device, such including a bed or other support with multiple inter-articulating surfaces having a built in pressure alarm, such including an arrangement of sensors, timer and switches extending between the device and a separate connected control module, for notifying when the patient is no longer supported upon the chair or recliner. A secondary aspect of the alarm is to notify the care giver when the patient has been supported in a static position to too long a period of time, thus necessitating repositioning in order to prevent the occurrence of bedsores and the like.

A further aspect of the present invention is to provide for dynamic therapeutic adjustment of the recliner device and which can include either slaved or independent repositionable drives (worm gear, scissor mechanism, etc.) incorporated into the seat and back supports. The repositionable drives are communicated with the control module in order to reconfigure the patient support device, such as timed intervals to correspond with patient repositioning, such as of particular value to immobile or mobility limited individuals.

BACKGROUND OF THE INVENTION

The prior art is documented with examples of patient monitory devices. A first example of these is the patient monitoring apparatus of EP 0 107 058 which includes a switching device and a monitoring device. The switching device includes a flexible base member having an aperture therethrough and sandwiched between two conductive members and covered with two cover members. When a patient lies on the switching device, the base member is deformed allowing the conductive members to close the circuit. The monitoring device includes a binary signal generator, a time delay which produces a signal when the signal generator has been operated for a predetermined time, a latching device, and an alarm signal generator and alarm control device for varying the nature of the alarm signal produced by the generator.

U.S. Pat. No. 9,253,891, to Williams, teaches a sensor pad that is adapted to be positioned on a patient's bed or chair as part of a monitoring system that provides a signal to a caregiver when the patient rises from the bed or chair and which also indicates when the pad is near failure. The sensor pad includes specialized contact plate patterning that creates zones on the sensor pad.

U.S. Pat. No. 7,666,151, to Sullivan et al., teaches a variety of devices, systems and methods for providing patient monitoring of such parameters as body motion, body position, respiratory rate and/or heart rate. A further version of a wireless patient monitoring system is depicted in U.S. Pat. No. 8,416,084, to Belmann et al., which teaches a variety of room based sensors disposed within room units and which relay collected data to a central controller.

SUMMARY OF THE INVENTION

The present invention teaches a patient supporting and reclining device, such also including a bed or other patient support having inter-articulating support surfaces and having a built in pressure alarm. In non-limiting embodiments, the device includes an arrangement of sensors, timer and switches extending between the device and a separate connected control module, for notifying when the patient is no longer supported upon the chair or recliner. As previously described, a secondary aspect of the alarm is to notify the care giver when the patient has been supported in a static position to too long a period of time, thus necessitating repositioning in order to prevent the occurrence of bedsores and the like.

Additional aspects of the present invention provide for dynamic therapeutic adjustment of the recliner device, and which can include either slaved or independent repositionable drives (worm gear, scissor mechanism, etc.) incorporated into the seat and back supports. The repositionable drives are communicated with the control module in order to reconfigure the patient support device, such as timed intervals to correspond with patient repositioning, such as of particular value to immobile or mobility limited individuals.

BRIEF DESCRIPTION OF THE DRAWINGS

Reference will now be made to the attached drawings, when read in combination with the following detailed description, wherein like reference numerals refer to like parts throughout the several views, and in which:

FIGS. 6-9 present a series of upright, partially reclined and fully reclined/lowered adjusted positions associated with the actuation of the first and second motor drives of the patient support and dynamic reclining/repositioning device;

FIG. 13 is an enlarged partial view of the coaxial tubular arrangement of FIG. 11 and better illustrating in cutaway the outer tube interfacing with the intermediate (second) gear drive for pivoting the seat back in combination with the inner coaxial tube interfacing with the end positioned (first) gear drive for pivoting the pair of rear and bottom roller supported legs.

DETAILED DESCRIPTION OF THE PREFERRED EMBODIMENTS

With reference now to FIGS. 1-13, the present invention provides a patient supporting and reclining device, such including a combination of features including each of contact (pressure or proximity) switches built into the device for determining the presence of an individual supported upon the device, along with an alarm for determining if the patient moves from the device. Additional functionality includes utilizing the timer function in order to instruct the caregiver when to reposition the (typically immobilized) individual.

The present invention also provides repositioning of the seat back and seat bottom, via the downwardly supporting legs, such including electric drive motors integrated into the device and which interface with a timer and alarm unit. The ability to reposition the device further assists in providing therapeutic relief to the patient and, again in the instance of patients of limited mobility or total immobility, further assists in preventing the occurrence of any of bedsores, pressure ulcers or the like. As will be further described, the dynamic repositioning functionality of the present device can also be programmed to respond to changes in patient posture, such as incrementally to the seat back and/or seat bottom.

Figure 1:
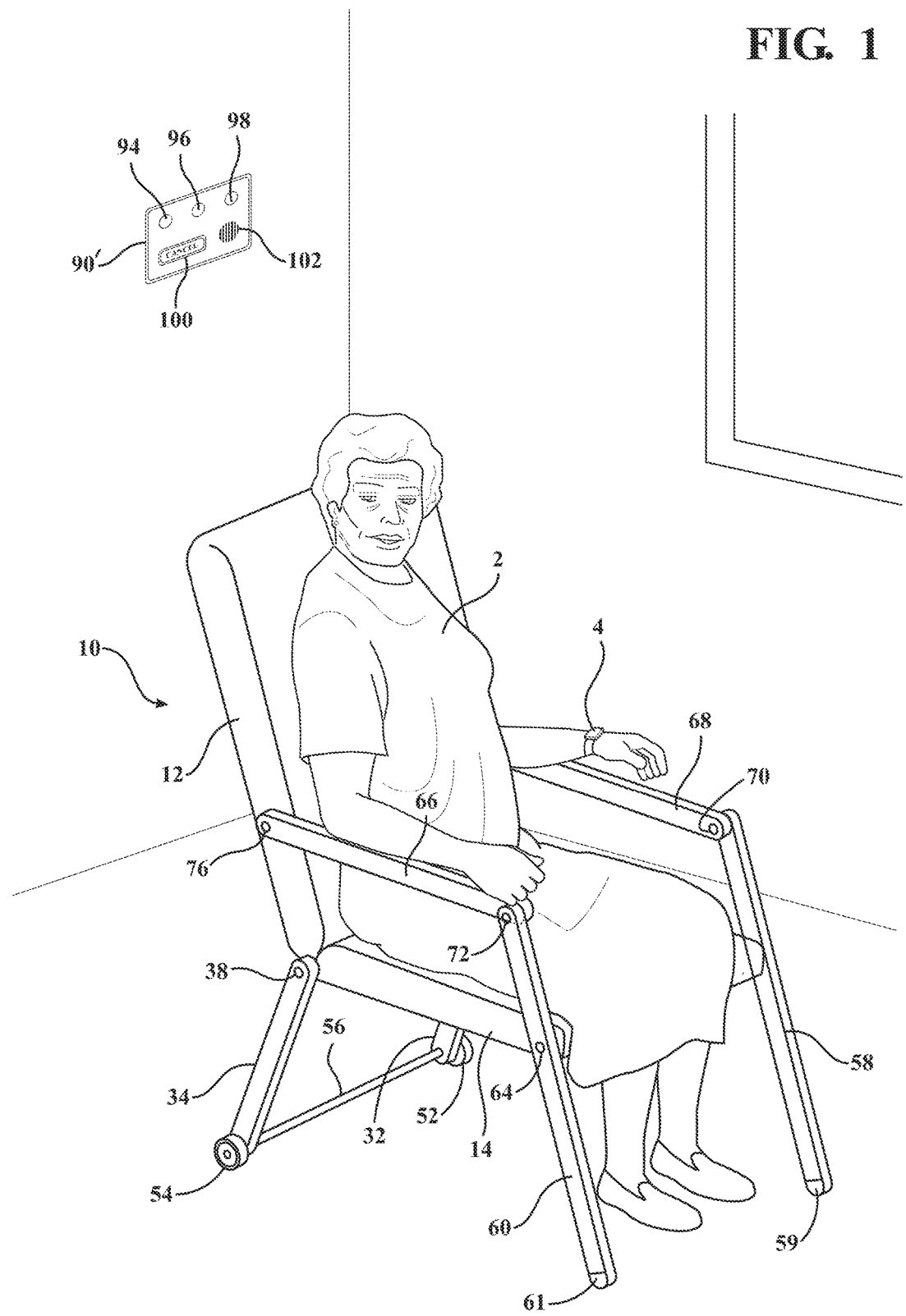
FIG. 1 is an environmental view of the patient support and reclining/repositioning device according to one non-limiting embodiment of the present invention.

Referring initially to FIG. 1, an environmental view is shown of the patient support and reclining/repositioning device, generally at 10, according to one non-limiting embodiment of the present invention and which, in combination with the several successive views, provides support to a patient 2. With further reference to each succeeding view, the reclining and dynamic support body provides a seat back 12 and a hingedly connected seat bottom 14.

Figure 2:
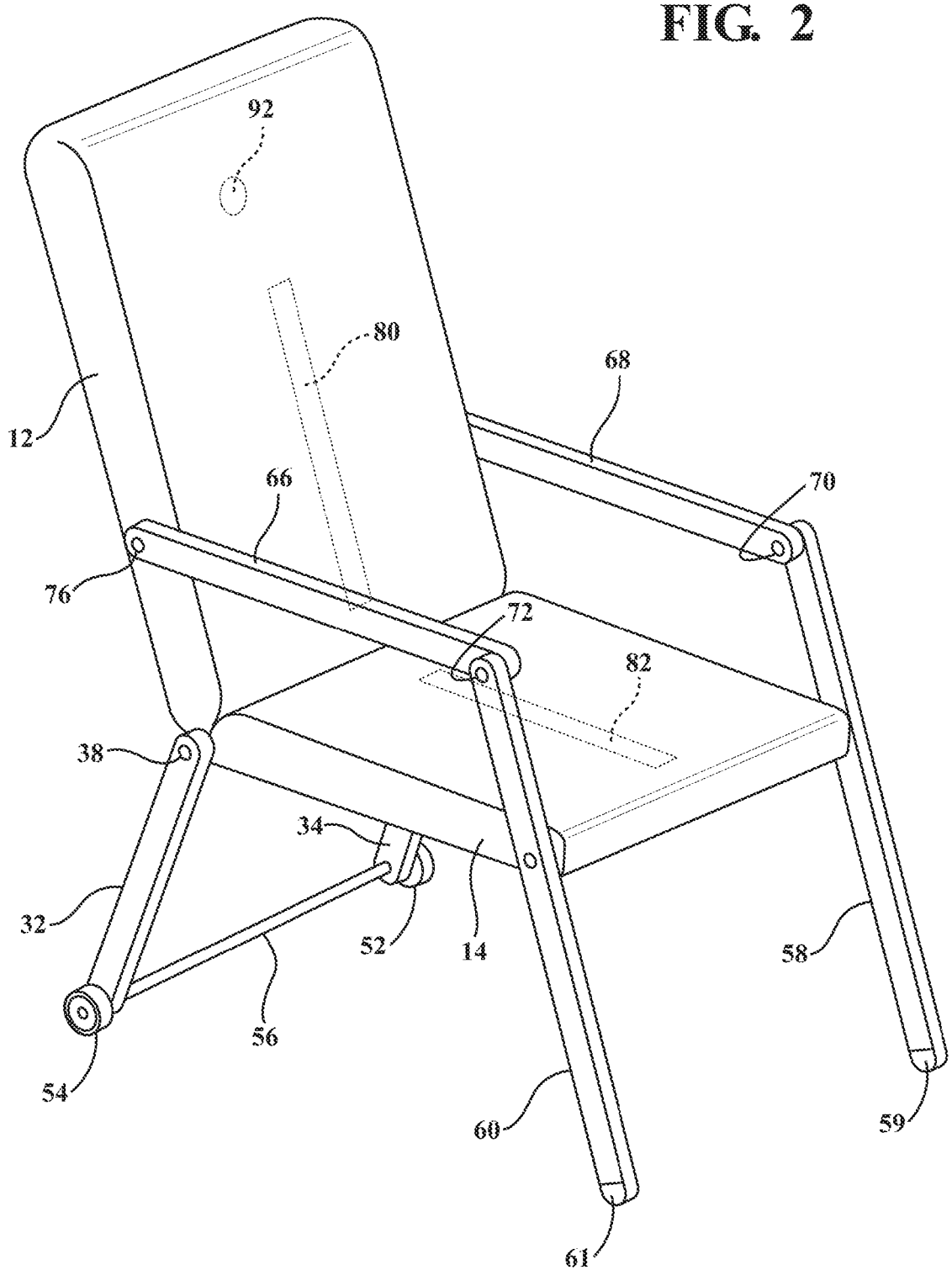
FIG. 2 is a perspective view of the device of FIG. 1 and better illustrating the pressure/proximity switches integrated into the fabric construction of the seat bottom and seat back components.
Figure 3:
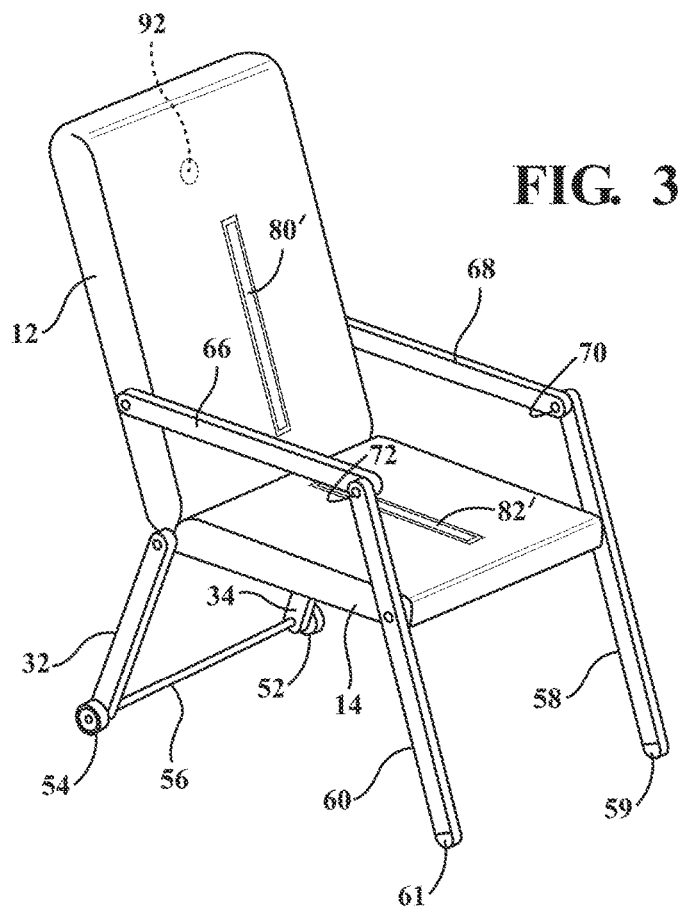
FIG. 3 is a related illustration to FIG. 2 and depicting a further variant of a device in which the pressure/proximity sensor switches are incorporated into surfacing strip materials applied to the exterior of the seat bottom and seat back cushions.
Figure 5:
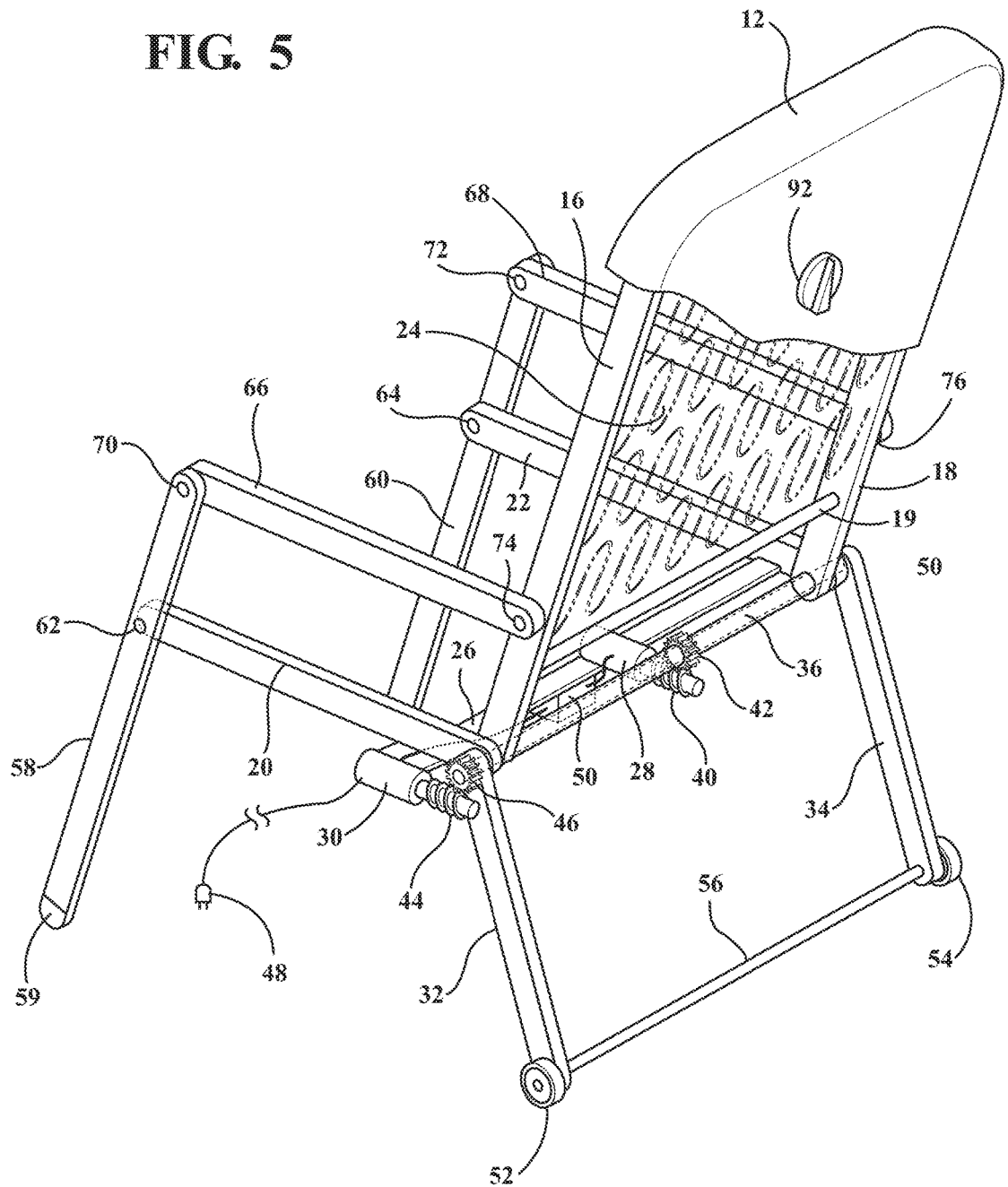
FIG. 5 is a rotated rear and partially cutaway perspective view of a patient support and dynamic reclining device according to a non limited variant and including first and second motor drives for respectively pivotally actuating the pair of rear legs and the seat back, both relative to the seat bottom (not shown)

For purposes of the present description, the seat back 12 and seat bottom 14 are depicted in FIGS. 1-3 as planar supports but can also include any rigid or cushion support such as including a frame and which incorporate spaced apart seatback frame members 16/18 and seat bottom members 20/22, as best shown in FIG. 5. As further shown in cutaway in FIG. 5, the seatback 12 further includes an interior support mesh or weave 24 (the same can be provided for the seat bottom 14). A separate cross wise extending and reinforcing support 19 is further shown at a lower intermediate location of the seatback sides 16 and 18 in order to provide additional support to the seatback structure.

The non-limiting structure of the recliner device (FIG. 5) further includes a crosswise extending support 26 interconnecting the spaced apart seat bottom members 20/22, such further supporting both a first (intermediate located) motorized gear drive 28 for hingedly actuating the seat back 12 and a second (side end located) motorized gear drive 30 for hingedly actuating a rear pair of legs, shown at 32 and 34.

A pair of outer 36 and inner 38 coaxially arrayed tubes or shafts (see also cutaway views of FIGS. 12-13) extend along the hinge established between the seat back and seat bottom. The first motorized drive 28 includes a worm gear 40 (see again in particular both FIGS. 5 and 12) which, upon activating, is rotated to engage a bevel gear 42 incorporated into the outer tube 36 for pivotally actuating the seat back 12. The second (outer edge) motorized drive 30 likewise includes a worm gear 44 in turn engaging an end supported bevel gear 46 integrated into the inner coaxial tube 38 for pivotally adjusting the seat bottom 12 again represented by sides 20/22 which secure to opposite rear ends of the inner tube 38, as best depicted in partial cutaway and phantom in FIG. 13 and which provides the pivot location for the rear legs 32/34.

The gear drives 28/30, such as which can be electric motor powered, can be activated by any suitable power source not limited to a DC wall plug, see for example at 48 in FIG. 5 in relation to selected motor 30. Alternatively, a power pack (see at 50) can be secured to a suitable location (such as to an underside of the crosswise support 26) and connected by a similar wire to selected motor 28. Each of the gear drives 28/30 can be actuated through the control unit features, as subsequently described below. It is further envisioned that either of common or separate switches can be provided for actuating each of the gear drives and associated linkages in the manner described and illustrated in FIGS. 6-9.

The rear pair of legs 32 and 34 each further include a roller, at 52 and 54 respectively, secured to bottom ends thereof. Additional structural stability is provided by a cross support 56 which provides a rotating axle for the rollers 52/54 and structurally supports the same to the bottom ends of the rear legs 32/34.

Figure 10:
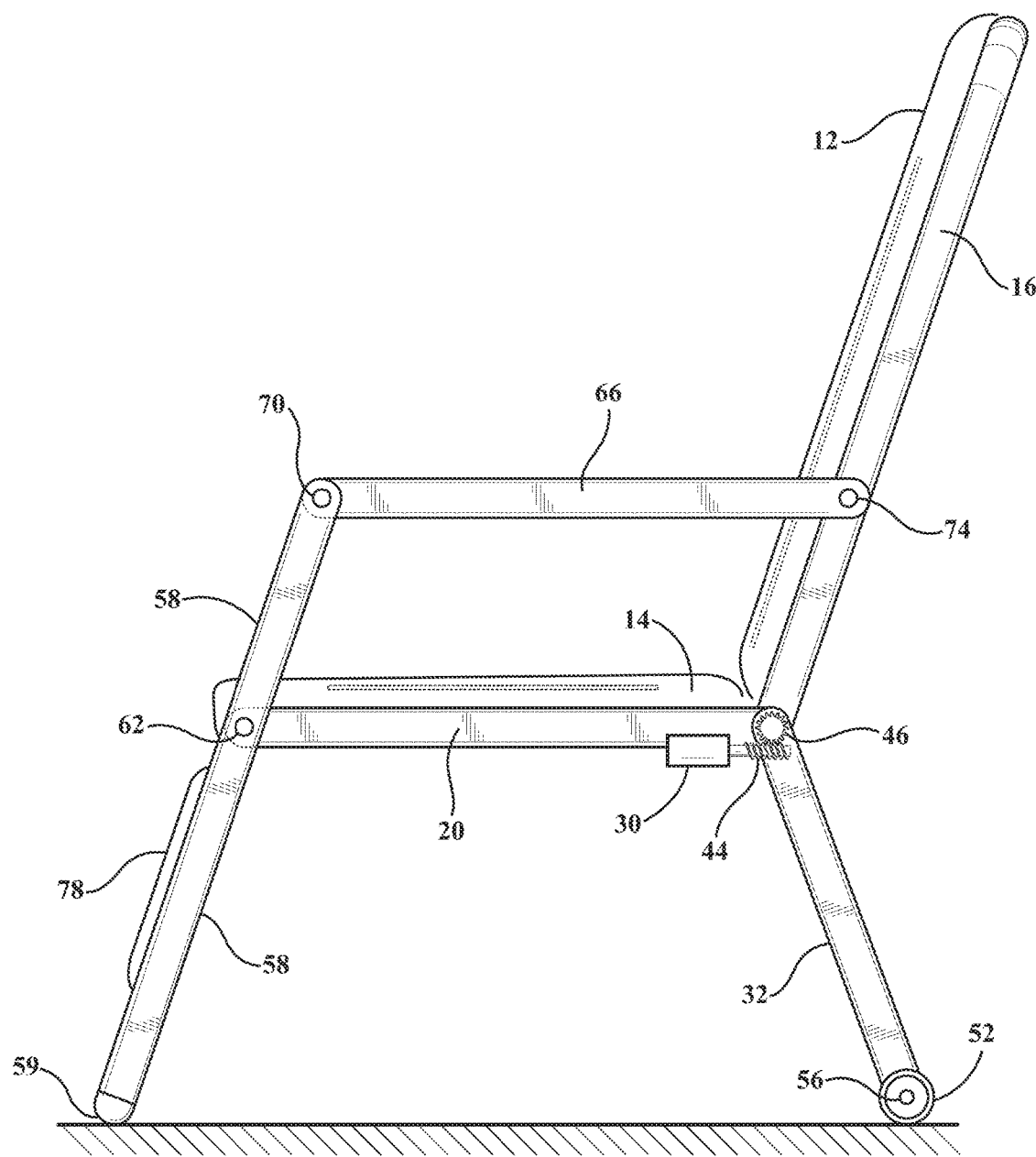
FIG. 10 is a side plan view of FIG. 5 and illustrating the outside edge positioned rear leg motor drive.
Figure 11:
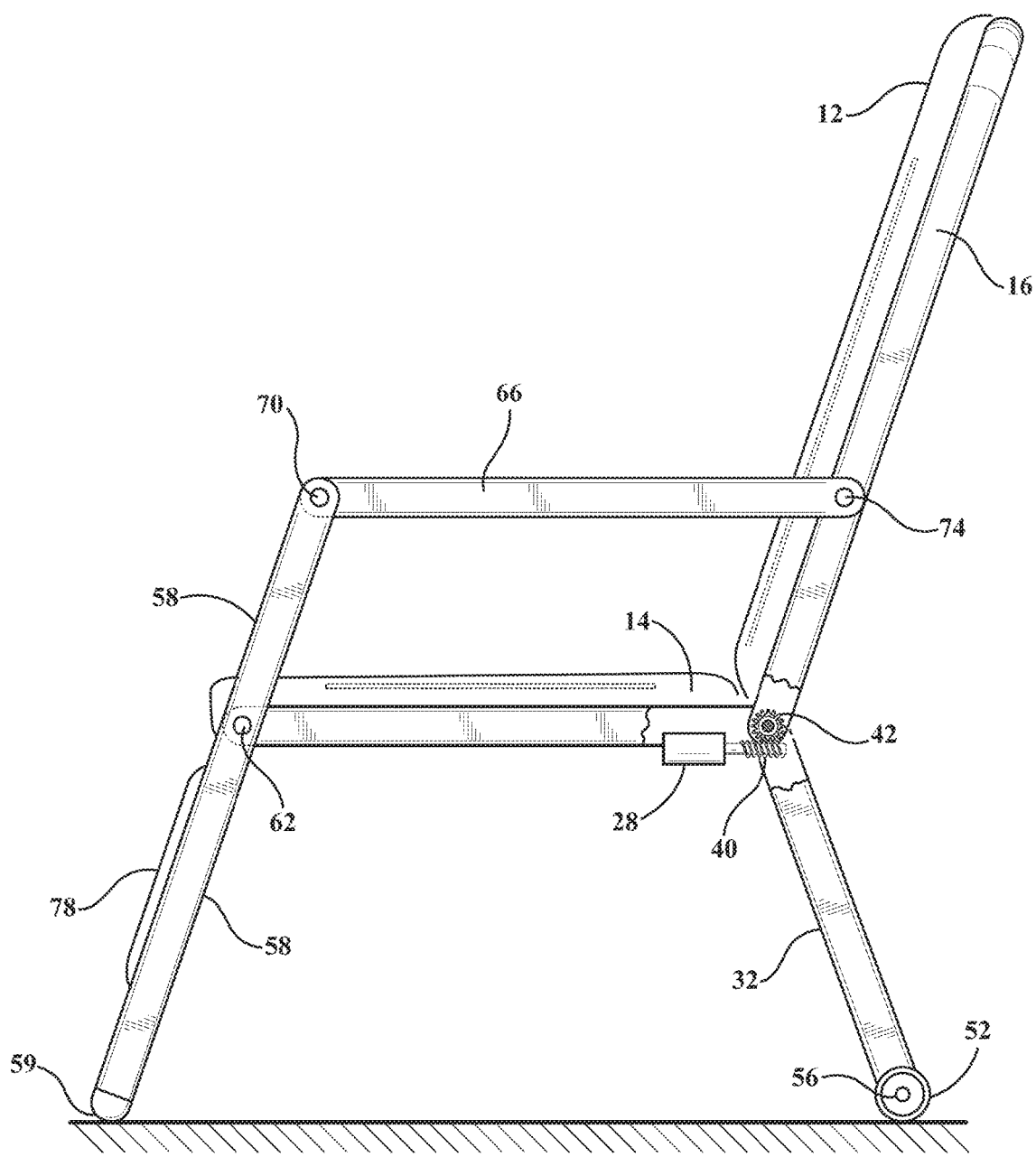
FIG. 11 is a succeeding side plan view of FIG. 9 and illustrating in cutaway the intermediate located seatback pivoting drive motor also shown in FIG. 5.
Figure 12:
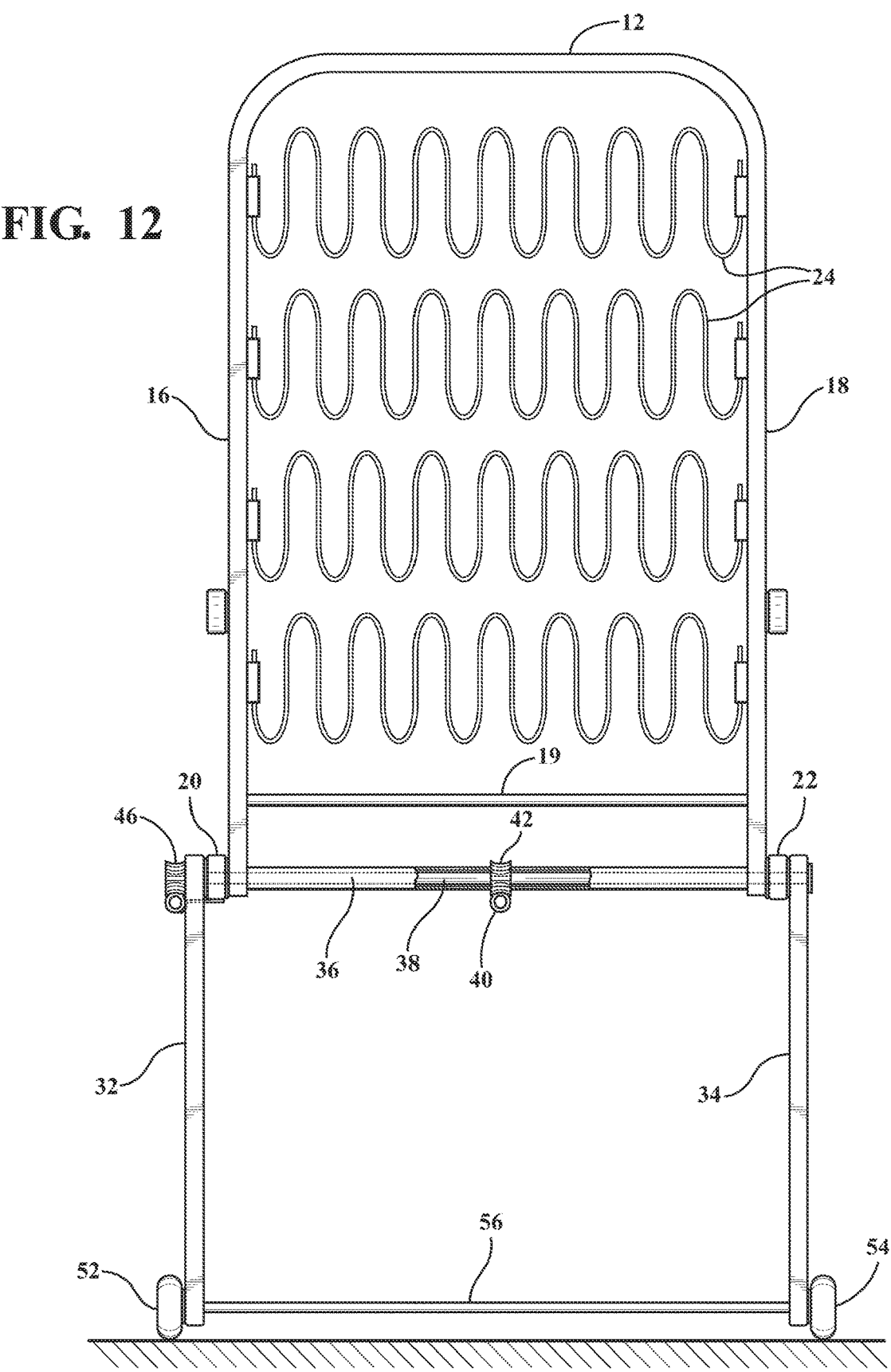
FIG. 12 is a rear plan view of the patient support and dynamic reclining device and illustrating the coaxial tubular arrangement interfacing with the first and second motor drives and defining the hinged interfaces for the seat back and rear legs relative to the seat bottom.

An additional pair of forward legs 58 and 60 are each hingedly supported, at intermediate locations 62 and 64, to forward corner locations of the seat bottom (as represented by the sides 60 and 22). A pair of armrest portions 66 and 68 are pivotally secured at forward ends 70 and 72 to upper ends of the forward legs 58/60, with rearward ends of the armrest portions pivotally securing to intermediate side locations 74/76 of the seat back. As best shown in FIGS. 10-11, a calf support and cushioning surface 78 is provided in crosswise extending fashion between the forward legs 58/60 and which provides additional structural support to the forward legs 58/60.

Having provided an overall structural explanation of the linkages associated with the reclining, device FIG. 2 provides a perspective view of the device of FIG. 1 and better illustrating an arrangement of pressure/proximity sensors or switches, see at 80 and 82, which are integrated into the fabric construction of the seat back 12 and seat bottom 14, respectively. The present invention contemplates, in a preferred embodiment, the sensors 80/82 being integrated into the cushion interior of the seatback and seat bottom.

FIG. 3 is a related illustration to FIG. 2 and depicts a further variant of a device in which the pressure/proximity sensor switches, further depicted at 80' and 82' are incorporated into surfacing strip materials applied to the exterior of the seat back and seat bottom cushions. The variant of FIG. 3 can include the sensor strips being applied to the exterior of a given existing static or repositionable recliner, such including any of adhesives, hook and loop fasteners or the like for supporting the sensor strips in position on the support surface.

Figure 4:
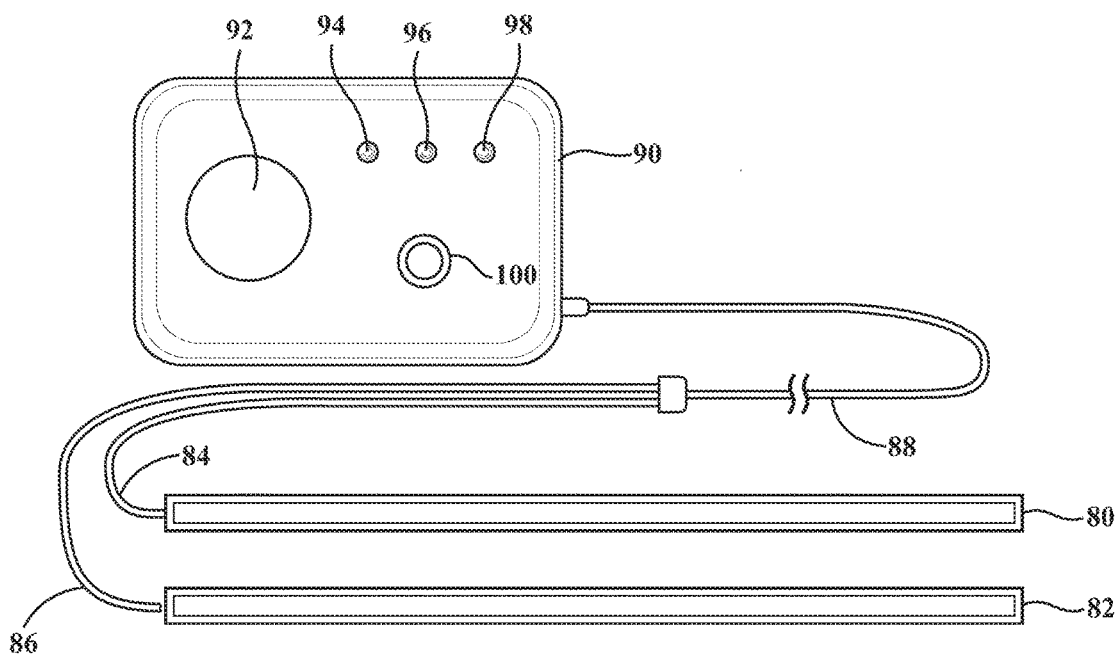
FIG. 4 is an illustration of a timer, reset and alarm unit according to one non-limiting variant which includes the attachable sensor/switch strips such as depicted in FIG. 3.

Without limitation, the sensors 80/80' and 82/82' may be incorporated into a waterproof covering and can also be provided in strip or tape form, such further depicted in FIG. 4 which illustrates a combination of the strips 80/82 with connecting wires 84 and 86, these combining into a common cable 88 which inputs to an alarm box or module 90. The module can be incorporated into a remote wall location (see as depicted at 90' in FIG. 1).

A variation of the module can also be incorporated directly into the seatback 12 and includes a timer knob 92 (see also in FIGS. 2, 3 and 5 projecting from the seatback 12 and which can be separated from the alarm box or module as depicted in FIG. 1 mounted to the wall). Other features of the alarm module 90 or 90' include a series of LED light indicators 94, 96, 98 and a cancel button 100 (different versions of which are depicted in the alarm modules presented in each of FIGS. 1 and 4).

The LED indicators can be illuminated according to any pattern, such as in order to determine if the sensors are engaged and according to what protocol. In one non-limiting protocol, the LED indicators 94, 96 and 98 can be represented by each of green, yellow and red lights, with the green light indicating that the system is activated and standing by, the yellow light further indicating the system is working with the patient supported in the chair, and the red light (such as which can work in combination with the alarm output) further indicating that the patient is no longer in contact with the chair or, in a separate protocol, that a determined time interval has expired requiring that the patient (still supported) needs to be repositioned.

Without limitation, the pressure sensor and tape can be constructed of a flexible material which, upon a set amount of pressure being applied which is representative of a person seated upon the seatback/seat bottom, will close a switch to reflect that the individual is being supported. As will be further described, the pressure switches can be configured to instruct the alarm to sound if pressure below a predetermined amount is sensed, such assisting in training proper posture (e.g. to dissuade slouching or the like). It is further envisioned that the processor components can dynamically interface with the sensor strips in order to vary the protocols in which the strips are activated, so as to account for variations in the performance environment within which the system is being utilized (e.g. individuals of lighter or heavier weight, individuals with lesser or greater degrees of individual mobility, and the like). The sensor strips 80/82 can also be separately communicated to the controller and so that they may individually trigger the alarm, such as in instance in which a patient is only partially unsupported by the recliner device.

The alarm box includes a micro chip in communication with the sensors 80/82, and can include an on/off switch (such as which can be integrated into the timer knob 92). Additional features can include a buzzer or speaker, see at 102 in FIG. 1, incorporated into the alarm box 90, such further including any of a piezo transmitter or the like which can be integrated into a single board processor (such as a Raspberry pi single board processor) which is integrated into the alarm box interior.

The processor can be communicated with a suitable power source (not limited to plug in or a Lithium ion power source), and further communicated, via a Bluetooth or wireless output transmitter, with a version of the assembly in which the tape sensors are separated from the alarm module (contrasting to FIG. 4) and in which alarm module transmitter is connected wirelessly to a receiver in operative engagement with the sensor tape (such as to notify if a user is not supported upon the recliner device or if a determined time interval has expired requiring the care giver to reposition the patient. Protocols built into the process can include the alarm sounding in instances in which the patient is not in contact with the pressure sensors/strips 80/82 for any determined time interval (including but not limited to programming the alarm to sound at no longer than 2-3 from pressure sensor contact with the person) and to discount incidences of momentary repositioning of the patient.

Other features include data capture capabilities incorporated into the processor for providing a history of patient support and repositioning cycles, such as in interconnecting fashion to a remote server including any of a computer processor (hard drive or laptop) or even a mobile application which can be wirelessly interfaced with the processor (such as via 4G, 5G wireless network and/or by any of Bluetooth® or other Near Field Communication (NFC) protocols.

Additional features include the chair tilt and recliner also being control by information inputs provided from a remote device not limited to any of a smart phone, smartwatch (see at 4 in FIG. 1 worn by the patient) or other input, such as which can detect the sleep patterns of the person, or any other physiological response or desired protocol, and so that the bed will automatically adjust according to the information, such as the chair changing from a reclining to a sitting position automatically upon the person awaking and upon the smart watch (such as which can integrate motion sensor technology) determining that the patient is now awake. The processor aspects can also include artificial intelligence capabilities, such as which adaptively memorize the pressure distribution of the patient and being able to track pressure distribution changes. This can also include the cancel or reset button in the controller also being operated by a similar button or tab integrated into the smartwatch or other mobile platform.

With reference to FIGS. 6-9, presented are a series of upright, partially reclined and fully reclined/lowered adjusted positions associated with the actuation of the first and second motor drives of the patient support and dynamic reclining/repositioning device. As previously described, the controller includes the timer and alarm output in communication with the arrangement of seatback 80 and seat bottom 82 sensors and the first 28 and second 30 motorized worm gear to bevel drives. The first seatback actuating drive 28 and second rear leg actuating drive 30 can be triggered separately or in combination so that the seat back and seat bottom are pivoted according to varying orientations. The bottom ends of the forward legs 58 and 60 can each include a rubberized or other skid resistant coating, see at 59 and 61 respectively, and which will prevent skidding of the front lower edges in contact with the floor location during controlled pivoting of the roller supported rear legs and seatback.

Upon triggering of the drive motors, whether by the caregiver actuating the control unit or by a processor output signal of the controller, the reclining device is thereby capable of pivoting according to any of the positions shown. The system operates in a first mode to issue an alarm signal upon either of the patient not being in contact with the proximity sensor or passage of a period of time in which the patient is supported in a static position.

Figure 6:
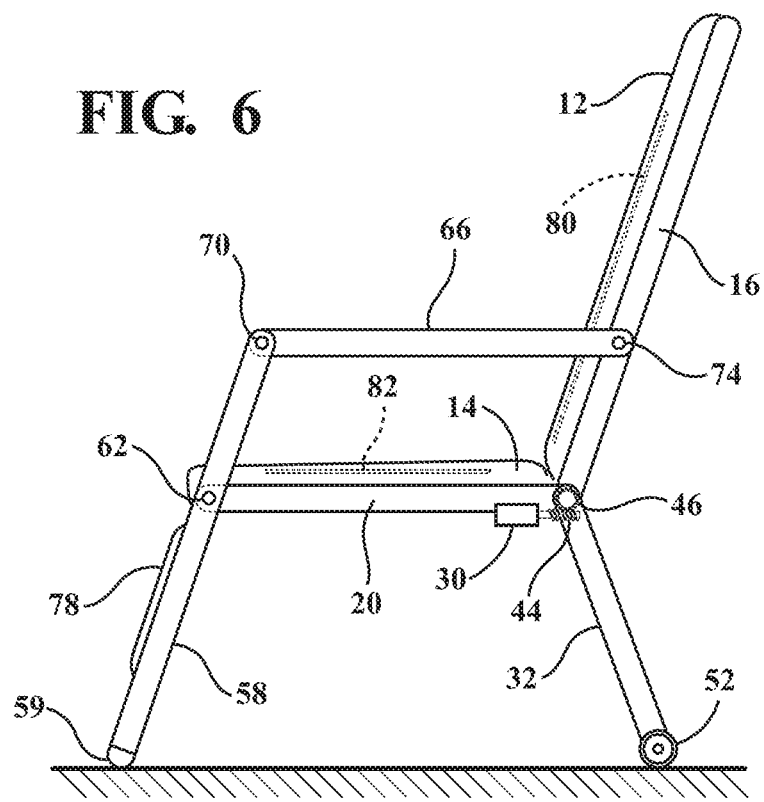
Figure 7:
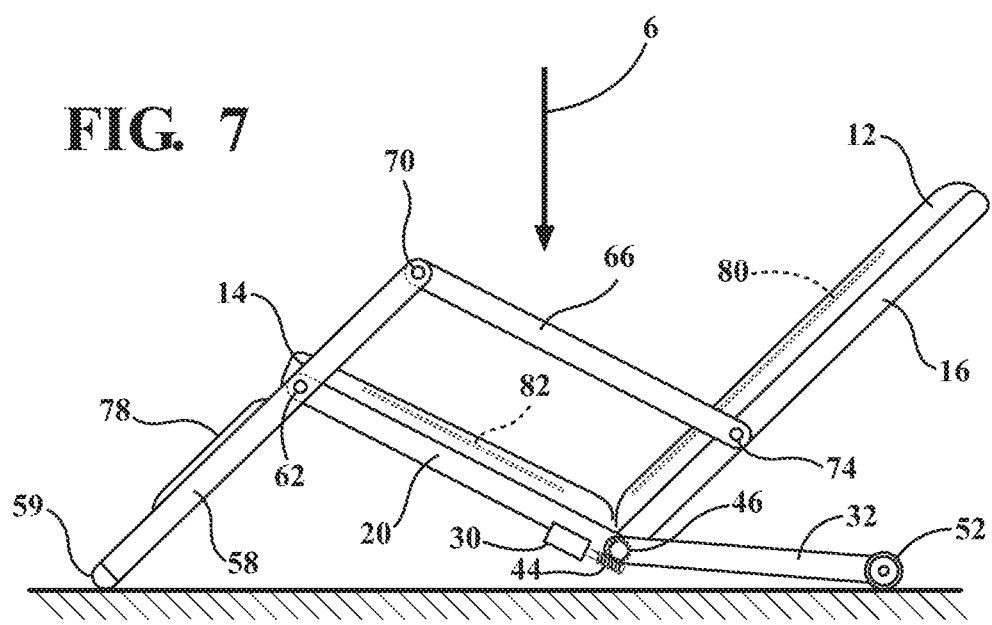

The controller can further operate in a second mode for actuating the motorized drives for repositioning the seat back, seat bottom, and rear pair of legs in order to reposition the patient between each of the sitting position of FIG. 6, the rear-leg pivoted and partially reclined position of FIG. 7 (such further including vertical arrow 6 which represents a pressure sensor acknowledged center of gravity being exerted by the weight of the patent upon the recliner device during actuation motion of the drive motors and in order to prevent tipping of the device), the modified reclined position of FIG. 8 in which the rear legs extend parallel to the seat bottom and the seat bottom establishes a greater acute angle with the forward legs, and the fully reclined position of FIG. 9 in which the patient can be repositioned in a substantially flattened arrangement corresponding to a standardized bed. Without limitation, the armrest linkages can also be fixed to prevent the forward legs from pivoting, thereby maintaining an angle between the patient's legs and the seat bottom, while imitating articulation to the seat back 12 and rear legs 32/34, both relative to the seat bottom 14.

The variants of the present invention also contemplate the ability of the pressure sensors to communicate with the controller/processor in such as fashion to enhance and augment the collection of data and diagnostic functionality, such as which can be stored in any processor including a Cloud based platform. In this manner, the supporting systems provide for data functionality based upon aggregating patient support information. Such functionality is intended to also provide for improved analysis and reporting of patient support, both in terms of medical records, health care billing and the like.

Consistent with the above description, a related variant of the patient support device includes the patient support body being provided by at least two separate platforms (again not limited to any of a bed, or other recliner or multi-hinged patient support platform which can converted between standard seating and reclined positions) and which is adapted for supporting different body portions of the patient. As previously described, a pressure sensor (according to any of the afore-described variants) is integrated into at least one of the platforms (not limited to those shown at 12 and 14 in the preceding illustrations).

In operation, the platforms are configured so as to move relative to the vertical directed center of gravity (again depicted at 6 in FIG. 7), which is exerted by the patient on the support, and as further communicated via the inputs from the pressure sensors (e.g. again at 80/82) to either motor drive 28/30 in communication with the platforms for altering a pressure distribution exerted both by and upon the patient. The platforms further again include any type of back and seat support, with pairs of front and rear legs being hingedly connecting to corner locations of the seat and, in combination with armrest portions 66/68 extending between the ends of the forward legs (58/60) projecting upwardly from the corner locations and intermediate locations of the back, defining a parallelogram shape (this defined as the rectangular profile established by the armrests 66/68 extending along top edges, the seat bottom 14, the seat back 12, and the uppermost portions of the forward legs 58/60 extending above the seat bottom 14), and visible on either side of the body (best shown in FIG. 2)

In this manner, simultaneous induced motion by the motor drive(s) 28 or 30 result in the back 32/34 and front 58/60 legs moving simultaneously and parallel to each other for controlling a recline motion. In an alternate operation, induced motion by the rear leg controlling (first) motor drive 28 on the rear legs alone results in rearward tilting of the chair shaped recliner orientation (again as best substantially shown in FIG. 7) without change in orientation of the front legs. As previously described, the motor drives 28/30 can be triggered by either of elapsing of the timer or in response to any shift in the patient posture, such adjustments including incremental changes in the seatback or seat bottom as directed by the controller processor, such as to further maintain both correct posture support as well as to maintain a correct center of gravity to avoid tipping over of the body.

Other features again include the provision of the controller 90 including again at least a timer (see with dial 92 built into the chair back) and an alarm output and being in communication with the pressure sensors and the motor drives. As further previously described, a time delay can be integrated into the processor aspects of the controller, such as to prevent occurrence of a false alarm notification resulting from a temporary change in a readout of the pressure sensor not conclusive of a patient no longer being in contact with the platforms (by example the patient shifting his or her weight temporarily so as to momentarily out of contact with the pressure sensors 80/82.

Additional features include, additional to integrating the sensors permanently into the fabric or other substrate of the recliner, also include providing the sensors as a tape like device constructed from a flexible material which can be adhered or otherwise secured to the exterior of the seat bottom and/or seat back. The data collection functionality incorporated into the processor and control unit may include data collection features associated with any of the duration and orientations associated with the patient support assembly. Other features include incorporating multiple sensors at different areas or zones of the chair, the sensors potentially having different sensitivity settings in order to assist in training proper posture.

Having described my invention, other and additional preferred embodiments will become apparent to those skilled in the art to which it pertains, and without deviating from the scope of the appended claim. This can include integrating the features of the alarm and repositioning system into other patient support devices not limited to beds (with upper, middle and lower mattress sections), cushioned wheelchairs, or the like. Other features can include substituting the separate motor and worm gear drives with a single motive generating component, such as which can be communicated with a scissor linkage or other suitable mechanism for actuating separately or in tandem the seat back and rear legs according to any desired orientation.

It is also envisioned that the sensors can be integrated into other forms for integration into the seatback and seat bottom, such including the use of channels of air tubes, such as in a mattress or other pressurized interior, and which can provide equivalent sensor indication to the pressure switches according to any of the operating modes. Such an arrangement can also provide for variations through alternating pressure induced into the patient supporting components and in order to provide massage functionality or the like.

I claim:
1. A patient support assembly, comprising:
    a patient support body having a seat back and a hingedly connected seat bottom;
    a patient proximity sensor integrated into at least one of said seat back and seat bottom;
    pairs of forward and rearward legs extending from said seat bottom and adapted to support said body upon a ground location;
    at least said rearward pair of legs being hingedly connected to said seat bottom, a roller incorporated into an extending end location of each of said rearward pair of legs;
    a first motorized drive for hingedly actuating said seat back relative to said seat bottom;
    a second motorized drive for hingedly actuating said rear pair of legs relative to said seat bottom;
    said forward pair of legs each being hingedly supported, at intermediate locations, to forward corner locations of said seat bottom, a pair of armrest portions pivotally securing at forward ends to upper ends of said forward legs, rearward ends of said armrest portions pivotally securing to intermediate side locations of said seat back defining a parallelogram shape on either side of the body, simultaneous induced motion by said motor drives resulting in said back and front legs moving simultaneously and parallel to each other for controlling a recline motion of said body; and a controller including at least a timer and an alarm output and being in communication with said sensors and said first and second motorized drives, said controller operating in a first mode to issue an alarm signal upon either of the patient not being in contact with said proximity sensor or passage of a period of time in which the patient is supported in a static position, said controller operating in a second mode for actuating said motorized drives for repositioning said seat back, seat bottom, and rear pair of legs in order to reposition the patient.

2. The patient support assembly of claim 1, further comprising a pair of outer and inner coaxially arrayed tubes extending along said hinge established between said seat back and seat bottom, said first motorized drive actuating said outer tube for pivotally adjusting said seat back, said second motorized drive actuating said inner coaxial tube for pivotally adjusting said rearward legs and, by relation, said seat bottom.

3. The patient support assembly of claim 1, each of said first and second motorized drives further comprising a worm gear drive powered by an electric motor secured to a housing supporting said drive.

4. The patient support assembly of claim 1, said timer further comprising a timer dial integrated into said seat back of said body and communicated with said controller.

5. The patient support assembly of claim 1, said controller further comprising a plurality of lights for determining each of the system activation, active with patient supported on said body, and alarm or timer expired situation associated with either of said first and second modes.

6. The patient support assembly of claim 1, said sensors each further comprising pressure switches integrated into a flexible tape layer, said tape layers being embedded within an interior of each of said seat back and seat bottom in a first installation, said tape layers being adhered to an exterior of each of said seat back and seat bottom in a second installation.

7. A patient support assembly, comprising:
a patient support body having a seat back and a hingedly connected seat bottom;
a patient proximity sensor integrated into each of said seat back and seat bottom;
pairs of forward and rearward legs extending from said seat bottom and adapted to support said body upon a ground location;
said rearward pair of legs being hingedly connected to said seat bottom, a roller incorporated into an extending end location of each of said rearward pair of legs, extending end locations of said forward legs each exhibiting a skid resistant surface in contact with a supporting floor location;
at least one motorized drive for hingedly actuating either of said seat back relative to said seat bottom and/or for hingedly actuating said rear pair of legs relative to said seat bottom; and
a controller including at least a timer and an alarm output and being in communication with said sensors and said first and second motorized drives, said controller operating in a first mode to issue an alarm signal upon either of the patient not being in contact with said proximity sensor or passage of a period of time in which the patient is supported in a static position, said controller operating in a second mode for actuating said motorized drives for repositioning said seat back, seat bottom, and rear pair of legs in order to reposition the patient said timer further comprising a timer dial integrated into said seat back of said body and communicated with said controller.

8. The patient support assembly of claim 7, said at least one motorized drive further comprising a first motorized drive for controlling pivoting of said seat back and a second motorized drive for controlling pivoting of said rearward legs and, by relation, said seat bottom.

9. The patient support assembly of claim 8, further comprising said forward pair of legs each being hingedly supported, at intermediate locations, to forward corner locations of said seat bottom, a pair of armrest portions pivotally securing at forward ends to upper ends of said forward legs, rearward ends of said armrest portions pivotally securing to intermediate side locations of said seat back defining a parallelogram shape on either side of the body, simultaneous induced motion by said motor drives resulting in said back and front legs moving simultaneously and parallel to each other for controlling a recline motion of said body.

10. The patient support assembly of claim 8, further comprising a pair of outer and inner coaxially arrayed tubes extending along said hinge established between said seat back and seat bottom, said first motorized drive actuating said outer tube for pivotally adjusting said seat back, said second motorized drive actuating said inner coaxial tube for pivotally adjusting said rearward legs and, by relation, said seat bottom.

11. The patient support assembly of claim 8, each of said first and second motorized drives further comprising a worm gear drive powered by an electric motor secured to a housing supporting said drive.

12. The patient support assembly of claim 7, said controller further comprising data capture capability not limited to any remote or Cloud based information and analytical storage pertaining to patient function and details of dynamic support and repositioning.

13. The patient support assembly of claim 7, further comprising said patient proximity sensors each being integrated into each of said seat back and said seat bottom.

14. The patient support assembly of claim 13, said sensors each further comprising pressure switches integrated into a flexible tape layer, said tape layers being embedded within an interior of each of said seat back and seat bottom in a first installation, said tape layers being adhered to an exterior of each of said seat back and seat bottom in a second installation.

15. The patient support assembly of claim 7, further comprising a smart device not limited to smart watch worn by the patient and, upon interfacing with said controller in response to a physiological response, operating in a third mode to reposition said body.

16. A patient support, comprising:
at least two platforms adapted for supporting different body portions of a patient;
a pressure sensor integrated into at least one of said platforms; and
said platforms moving relative to a directed center of gravity adapted to being exerted by the patient on the support and as further communicated via inputs from said pressure sensor to a motor drive in communication with said platforms for altering a pressure distribution exerted either by or upon the patient; and
said platforms further including a back support and a seat, pairs of front and rear legs hingedly connecting to corner locations of said seat and, in combination with armrest portions extending between ends of said forward legs projecting upwardly from said corner locations and intermediate locations of said back, defining a parallelogram shape on either side of the body, simultaneous induced motion by said motor drive resulting in said back and front legs moving simultaneously and parallel to each other for controlling a chair recline motion.

17. The patient support of claim 16, further comprising a controller including at least a timer and an alarm output and being in communication with said pressure sensors and said motor drives, a time delay integrated into said controller to prevent a false alarm notification resulting from a temporary change in a readout of the pressure sensor not conclusive of a patient no longer being in contact with said platforms.

* * * * *